(12) United States Patent
White

(10) Patent No.: US 12,091,649 B2
(45) Date of Patent: Sep. 17, 2024

(54) ASEPTIC YEAST TRANSFER APPARATUS AND METHOD

(71) Applicant: White Labs, San Diego, CA (US)

(72) Inventor: Chris White, San Diego, CA (US)

(73) Assignee: WLDNA, LLC, Asheville, NC (US)

( * ) Notice: Subject to any disclaimer, the term of this patent is extended or adjusted under 35 U.S.C. 154(b) by 309 days.

(21) Appl. No.: 17/408,337

(22) Filed: Aug. 20, 2021

(65) Prior Publication Data

US 2023/0055476 A1 Feb. 23, 2023

(51) Int. Cl.
*C12M 1/00* (2006.01)
*C12C 11/02* (2006.01)

(52) U.S. Cl.
CPC ............. *C12M 23/14* (2013.01); *C12C 11/02* (2013.01); *C12M 29/04* (2013.01); *C12M 29/20* (2013.01)

(58) Field of Classification Search
CPC ................................ C12C 11/02; C12M 23/14
See application file for complete search history.

(56) References Cited

U.S. PATENT DOCUMENTS

| 2,571,893 | A | | 10/1951 | Kendall |
| 3,946,780 | A | * | 3/1976 | Sellers ............... B65D 51/1616 426/8 |
| 6,070,728 | A | | 6/2000 | Overby et al. |
| 2014/0367299 | A1 | * | 12/2014 | Dobel ..................... B32B 27/34 206/524.2 |
| 2016/0298810 | A1 | | 10/2016 | Maggiore |
| 2020/0115666 | A1 | * | 4/2020 | Goral ..................... C12M 99/00 |

FOREIGN PATENT DOCUMENTS

| EP | 0542089 A1 | 11/1992 |
| WO | 2017191192 A1 | 11/2017 |

* cited by examiner

*Primary Examiner* — Jonathan M Hurst
(74) *Attorney, Agent, or Firm* — Temmerman Law; Mathew J. Temmerman

(57) ABSTRACT

A yeast storage and transfer vessel having semi-permeable materials and a method for transfer of liquid yeast to a fermentor using said vessel and a peristaltic pump. In some embodiments, one or more opening(s) may include a port and valves and/or filters allowing the egress of carbon dioxide and other fermentation gases out of the yeast vessel. The bag storage vessel materials may also include semi-permeable materials. The herein disclosed apparatus and method permit the sterile transfer and mixing of yeast and/or fermentation product into a variety of fermentors, in addition to sterile pumping action in the reverse direction.

11 Claims, 7 Drawing Sheets

ASEPTIC YEAST TRANSFER APPARATUS AND METHOD

TECHNICAL FIELD

The present invention relates to a yeast storage and transfer vessel having semi-permeable materials and a method for transfer of liquid yeast to a fermentor using said vessel and a peristaltic pump. In some embodiments, one or more opening(s) may include a port and valves and/or filters allowing the egress of carbon dioxide out.

BACKGROUND

Liquid yeast transfer containers or vessels known in the art tend to be cumbersome in size, expensive, and must be deconstructed for sterilization after each use. In contrast, the present invention relates to a yeast transfer and storage vessel that is structurally streamlined and adapted for use with industrial fermentors of a variety of dimensions. Further, said apparatus and methods disclosed herein are adapted for use with a variety of yeast strains, particularly those with a low tolerance for contamination. In addition, the present yeast vessel is not a permanent, rigid structure, but rather is made from flexible, structurally elastic materials.

Yeast storage and transfer containers known in the art include, for example, containers with simple polyurethane, rigid walls that lack the capacity to mediate the unidirectional efflux of carbon dioxide. Yeast storage and transfer containers known in the art may also include laminated or coated yeast containers comprised of a single layer of polyvinylidene chloride or two layers of polyethylene. Polyethylene and polyvinylidene chloride are coextruded in another type of yeast container known in the art, which also lacks the capacity to mediate the unidirectional efflux of carbon dioxide. Fermentation locks known in the art include those with a fitment or cap sealed into an opening of a plastic yeast vessel. These prior art systems may also include a snap-type cap composed from any nonporous material including plastic or polyethylene.

Microorganisms which may adulterate the fermentation process include viruses, fungus, and bacteria including but not limited to examples such as wild yeast, acetic acid bacteria and lactic acid bacteria. Upon contamination of a yeast transfer vessel, said microorganisms will grow and divide, producing secondary metabolites that disrupt the flavor, color, and viscosity of fermentation product. Further, plaque-forming bacteria can accumulate in fermentors, brewing lines, and the like, creating self-propagating biofilms. Said biofilms may be difficult to eradicate, and ultimately can impact multiple generations of batched fermentations if aseptic yeast transfer procedures are not observed.

Filters in the art have been employed to reduce the incidence of such contamination events, often providing a mechanical or temperature-sensitive means of sterilizing surfaces where contamination is introduced. However, the effective employ of such filters or valves has been largely limited to mechanical sieves that filter out large bacterial aggregates. The present invention optimizes this feature, provide micro-scale filtration in the context of anoxic liquid yeast transfer.

Another common contaminant in the production of beer, wine, and other spirits is moisture. Prior art systems have utilized chemical means of abstracting water from the air during yeast transfer, but this approach often contributes to contamination rather than providing a remedy. To address this issue, the present invention includes unidirectional materials that restricts ingress of water into the yeast vessel. Thus, in contrast to the prior art, it is a particular object of the present invention to provide an improved sterilizable yeast vessel and method for use of such vessel in the storage and transfer of liquid yeast to a fermentor.

SUMMARY

It is a first objective of the present invention to provide an aseptic and efficient means of transferring liquid yeast to a fermentor.

It is a second objective of the present invention to provide a yeast vessel with optimized layering and filtration such that unidirectional egress of carbon dioxide is provided.

It is another objective of the invention to maintain an anoxic (i.e., low oxygen) environment during yeast transfer, thereby maximizing ethanol fermentation via anaerobic respiration while preserving cell viability.

It is yet another object of the invention to provide a more facile means of labeling yeast storage vessels, in addition to providing yeast vessel-specific information regarding cell count and the like.

It is another object of the invention to provide an aseptic yeast transfer method that may be replicated following hundreds of pumping cycles.

It is another objective of the invention to minimize contamination from the brew pump itself. This has been accomplished in the prior art by minimizing the number of necessary motor components, while ensuring said components remain completely isolated from the brewery line interior, as is the case with the peristaltic pump utilized in the below described invention.

It is another objective of the invention to enhance ease of use and portability of aseptic yeast transfer systems including with fermentors of varying size and complexity.

In some embodiments, the yeast vessel includes a yeast connection means and yeast storage means. The yeast storage means periphery may include laser perforations in some embodiments. In some examples, the yeast connection means includes at least one screw-type or snap-type port adapted to reseal the yeast vessel under sterile conditions. Further, the port may permit efflux of carbon dioxide in some embodiments. In some embodiments, the yeast vessel connection means includes a cap adapter and/or a unidirectional valve operably engaged with a port. In some examples, the yeast storage means is adapted to store a quantity of liquid yeast ranging between 500 ml and 3 L, preferably between 1 L and 2 L.

In other embodiments, the port defines at least one opening in the yeast vessel, and includes a filter in sealing engagement with the port. In some embodiments, the filter is adapted to support sterile transfer of liquid yeast to a fermentor under a wide range of temperature and pressure conditions. In some examples, the yeast vessel filter includes temperature-resistant, pressure-resistant, chemically resilient, and/or electrochemically resilient materials, thereby supporting sterile transfer of liquid yeast to a fermentor.

In still other embodiments, the yeast storage means includes a yeast storage means nonporous top surface and bottom surface with a first opening in said top surface. In some embodiments, a valve and/or filter disposed over said first opening allows escape of fermentation gases from said yeast vessel, said first opening having a Gurley porosity in the range of 2 to 120 seconds and disposed such that the egress of all gases from said yeast vessel during fermentation must pass through said first opening or a second opening in said top surface. In some embodiments, a liquid inlet means is disposed over said second opening, permitting liquid ingress into said yeast vessel. In some embodiments, a bottom opening in said bottom surface includes a liquid outlet means disposed over said bottom surface opening. Said liquid outlet means provides a liquid outlet from the yeast vessel. Finally, the yeast storage means may include a cap adapter providing a reversible means of opening and closing the valve.

In some embodiments, the cap adapter provides a reversible means of opening and closing the unidirectional valve. In other embodiments, the yeast storage means includes an external structural layering including 6 mil PET laminate. In other embodiments, the clear low density polyethylene (LDPE) comprises high oxygen transmission rate (OTR) materials having a transmission rate of at least 80 cc/[100 in^2–day] materials. In some embodiments, the walls of the yeast storage means include resilient and low-specific heat materials, said materials adapted for reliable use after hundreds freeze-thaw cycles and after exposure to a wide range of high pressure and low pressure conditions. In some embodiments, a filled yeast vessel includes at least 1 billion yeast cells/ml, preferably 2 billion yeast cells/ml. In other embodiments, a filled yeast vessel provides a yeast pitch rate of at least 1 million cells/ml, preferably at least 7 million cells/ml.

In some embodiments, an exterior wall of the yeast storage means serves as a resilient surface for direct ink printing and/or adhesive labeling, including the printing of QR codes and cell count information specific to each yeast vessel. In other embodiments, the walls of the yeast storage means include a material selected from the group consisting of polyurethane, laminated polyethylene, polyolefin, ethylene-vinyl acetate copolymer, polyvinylidene chloride, and/or a coextrusion of polyethylene and polyvinylidene chloride.

In some embodiments, a yeast pitching method includes the steps of connecting an injector to a brewery line between the fermentor and a peristaltic brew pump, fixing a sterile connection tube to the peristaltic brew pump, connecting a cap adapter to the yeast connection means and opening the valve, homogenizing the yeast following connection of the cap adapter to the yeast connection means, engaging the peristaltic brew pump in the forward flow direction in order to transfer the yeast into the brewery line, engaging the peristaltic brew pump in the reverse flow direction to back flush the yeast vessel, and re-engaging the pump in the forward flow direction in order to transfer the yeast back into the brewery line. When these steps are complete, the valve may be closed, and the brewery line may be removed.

In some embodiments, the above steps are performed in the reverse order such that a fermentation product is recovered from the fermentor, enabling packaging and/or analysis of said fermentation product. In some embodiments, wherein isopropyl alcohol is used to sterilize the yeast connection means and other surfaces throughout the pitching process, and wherein the rollers utilized in the peristaltic brew pump are optimized to enhanced wort aeration and transfer time. In other embodiments, fermentation product and/or liquid yeast may be transferred from the peristaltic brew pump to an empty yeast vessel within a hood.

In some embodiments, the cap or valve may be manually modulated to homogenize liquid yeast in a yeast vessel. In other embodiments, the homogenizing step is accomplished by re-engaging the pump in the forward direction. In some embodiments, a hose end of the injection point may be reversibly fixated to the peristaltic brew pump with a zip tie, clamp, or the like.

These and other advantages and features of the present invention are described with specificity below so as to make the present invention understandable to one of ordinary skill in the art.

DESCRIPTION OF THE DRAWINGS

The present invention is more particularly described with reference to the following drawings, in which.

DETAILED DESCRIPTION OF THE INVENTION

In general, the yeast vessel 10 of the present invention provides a modular and aesthetic means of injecting liquid yeast inline into a fermentor. In some embodiments, the user may draw "green" or fresh wort from the brewery line 48 into a yeast vessel 10, and then back into the brewery line if desired. In some examples, the yeast vessel 10 and method of injecting yeast form a closed, aseptic system benefiting from improved mixing of the yeast and enhanced quality of the fermentation product. In some embodiments, a peristaltic brew pump 44 is utilized to ensure a closed system and efficient transfer of the liquid yeast.

Figure 1A:
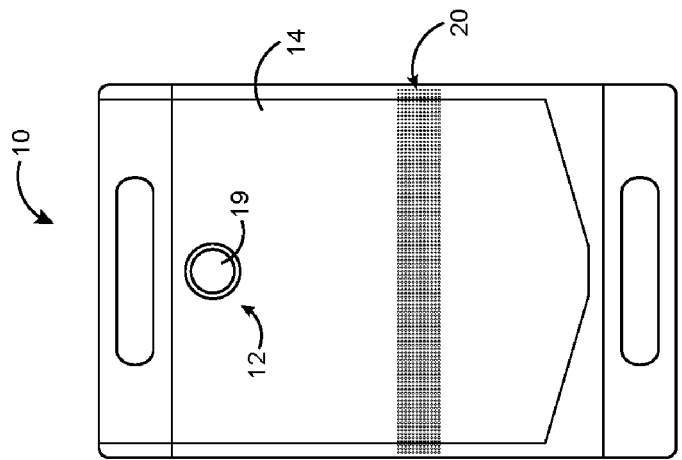
FIG. 1A depicts a yeast vessel top view including yeast vessel connection means, yeast vessel storage means, handles, and laser perforations.

In the preferred embodiment, the yeast vessel 10 of the present invention includes a yeast storage means 14 and a yeast connection means 12 capable of facilitating aseptic yeast transfer of liquid yeast to a fermentor 70, wherein the yeast storage means 14 is preferably a soft sided bag. In some embodiments, as shown in FIG. 1A, the yeast vessel includes a yeast vessel connection means 12 (e.g., including a first opening 18 and a second opening 19 in some embodiments). FIG. 1A also depicts central laser perforation and various resilient packaging features that provide a system adapted to use under repeated fluctuations in pressure and temperature. In another embodiment, the yeast vessel 10 includes a yeast connection means and yeast storage means adapted to particular use with beer, wine, or other particular spirits. Notably, the yeast storage means periphery may include laser perforations that blends multiple layers of film to achieve a high level of OTR (e.g., breathability), sealability, and strength, while maintaining a closed clean environment for the product.

Figure 1B:
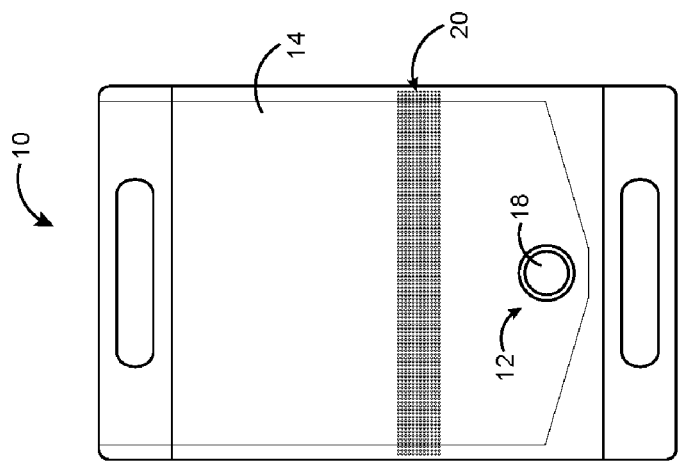
FIG. 1B depicts a yeast vessel bottom view including yeast vessel connection means, yeast vessel storage means, handles, and laser perforations.

In some examples, the yeast connection means includes at least one port adapted to reseal the yeast vessel 10 under aseptic conditions, permitting efflux of carbon dioxide and various fermentation gases. In some embodiments, the yeast vessel connection means includes a cap adapter and/or a unidirectional valve 22 operably engaged with the port. In some examples, the yeast storage means is adapted to store a quantity of liquid yeast ranging between 500 ml and 3 L, preferably between 1 L and 2 L. Notably, the unidirectional valve 22 and filter 24 are optional features and are not depicted in FIG. 1A nor FIG. 1B. FIG. 1B depicts a yeast vessel bottom view including yeast vessel connection means, yeast vessel storage means, and laser perforations.

In other embodiments, the port defines at least one opening in the yeast vessel 10 and may include a filter in sealing engagement with the port, said filter adapted to support an aseptic transfer of liquid yeast to a fermentor under a range of temperature and pressure conditions. In some embodiments, the port can have a rim or shoulder shaped to protrude either outward or inward from the storage means for snapping a cap either around the outside or on the inside of the port. In some examples, the yeast vessel filter includes temperature-resistant, pressure-resistant, chemically resilient, and/or electrochemically resilient materials, thereby supporting sterile transfer of liquid yeast to a fermentor.

Figure 2:
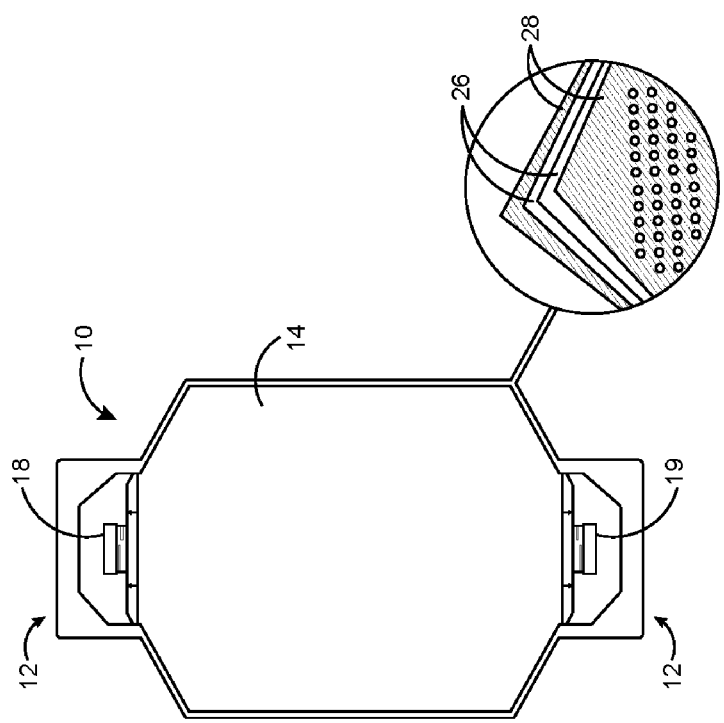
FIG. 2 an elevational view of yeast vessels in use including two openings, in addition to internal and external structural layering.
Figure 3:
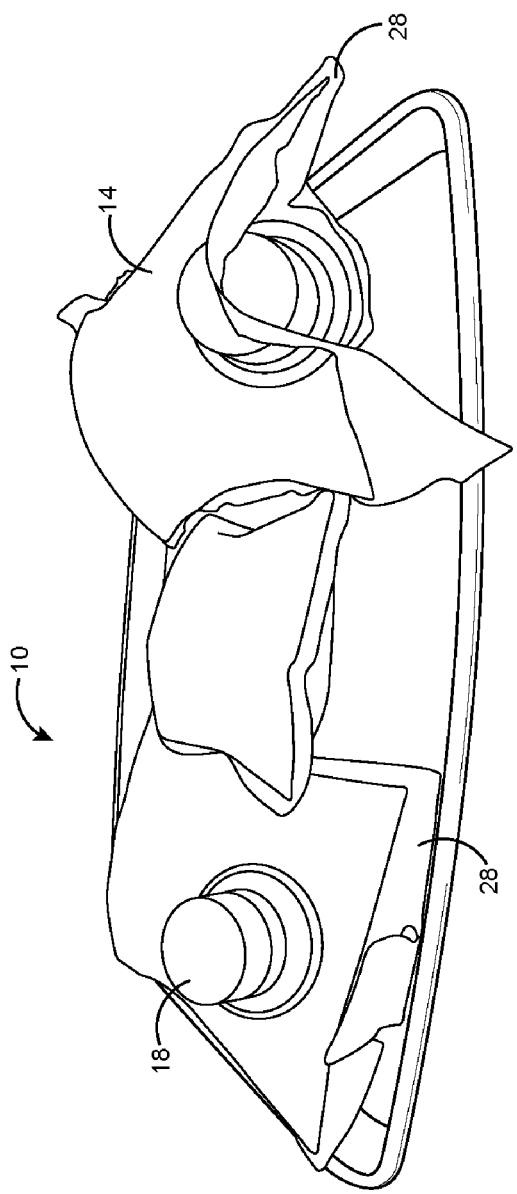
FIG. 3 is an elevational view of the yeast storage means of the present yeast vessel including the first and second openings and the external structural layerings.

In the preferred embodiment, as shown in FIG. 2, the yeast storage means 14 and yeast connection means 12 are capable of facilitating aseptic yeast transfer to a fermentor 70. The yeast vessel 10 of FIG. 2 also includes a yeast storage means internal structural layering 26 and yeast storage means external structural layering 28. In some embodiments, these elements are optimized to function under various temperature and pressure, and/or may include a color change film indicating appropriate transport and storage temperature. FIG. 2 also shows the first opening 18 and second opening 19 oriented at opposing ends of the yeast vessel 10. In further embodiments, an emergency relief valve may be provided proximate to the first opening to permit spontaneous gas release. Similarly, FIG. 3 shows the yeast storage means 14, the yeast vessel connection means first opening 18, and the yeast storage means external structural layering 28.

In still other embodiments, the yeast storage means includes a yeast storage means nonporous top surface and bottom surface with a first opening 18 in said top surface. In some embodiments, a valve 22 and/or filter 24 disposed over said first opening allows escape of fermentation gases from said yeast vessel, said first opening 18 having a Gurley porosity in the range of 2 to 120 seconds and disposed such that the egress of all gases from said yeast vessel during fermentation must pass through said first opening or a second opening in said top surface. In some embodiments, a liquid inlet means is disposed over said second opening 19, permitting liquid ingress into said yeast vessel when desired by a user. In some embodiments, a bottom opening in said bottom surface includes a liquid outlet means disposed over said bottom surface opening. Said liquid outlet means provides a liquid outlet from the yeast vessel 18. Finally, the yeast storage means may include a cap adapter providing a reversible means of opening and closing the valve. In some embodiments, the first and/or second openings are fitted to a screw-type cap. In other embodiments, additional screw or clamp-type attachment means are provided proximal to the screw-type cap, providing modular fastening to various brewery line fittings.

Figure 4:
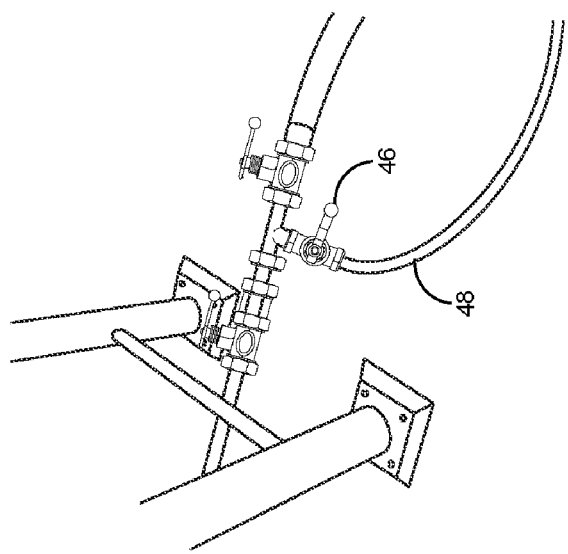
FIG. 4 is an elevational view of the brewery line and injector in a connected configuration during a liquid yeast transfer.

In some embodiments, the yeast storage means is configured in a closed system with various elements including the connection means first opening, peristaltic brew pump body, pump initiation switch, peristaltic brew pump, brewery line, and injector (or any sanitary connection) 46. FIG. 4 shows that the injector (or any sanitary connection) 46 and brewery line 48 may be operably connected in a closed system during a liquid yeast transfer event, thereby ensuring a sterile environment. This setup also allows for a user to pull wort out of the brewery line 48. In the preferred embodiment, the above components are assembled into a modular system, wherein the interconnected parts are compatible across multiple product lines. In some examples, the above components provide a means of collecting and storing harvested yeast for testing and re-pitching via the above modular system. In some embodiments, the internal roller components of the peristaltic pump 44 are customized in order to minimize crushing action, maximize aeration, or the like. In other embodiments, a clamp 50 is utilized (i.e., a horseshoe clamp) and/or rubber grippers may be used to secure a pass-through style brewery line 48 and lock the brewery line 48 into a state amendable to quick release of the pump configuration.

In some embodiments, the cap adapter provides a reversible means of opening and closing the unidirectional valve. In other embodiments, the yeast storage means includes an external structural layering including 6 mil PET laminate. In other embodiments, the clear LDPE comprises high OTR materials. In some embodiments, the walls of the yeast storage means include resilient and low-specific heat materials, said materials adapted for reliable use after hundreds of cycles and after exposure to a range of pressure conditions. In some embodiments, a filled yeast vessel 10 includes at least 1 billion yeast cells/ml, preferably 2 billion yeast cells/ml. In other embodiments, a filled yeast vessel 10 provides a yeast pitch rate of at least 1 million cells/ml/° P, preferably at least 7 million cells/ml/° P. In other embodiments, the yeast vessel 10 includes a storage means 14 that itself is comprised of unidirectional materials, for example materials permitting the efflux of carbon dioxide. If said materials are used for the body of the vessel, one may omit the unidirectional filter or valve at an opening 18 of the vessel and continue to benefit from the unidirectional filtering capacity of the yeast vessel 10.

Figure 5:
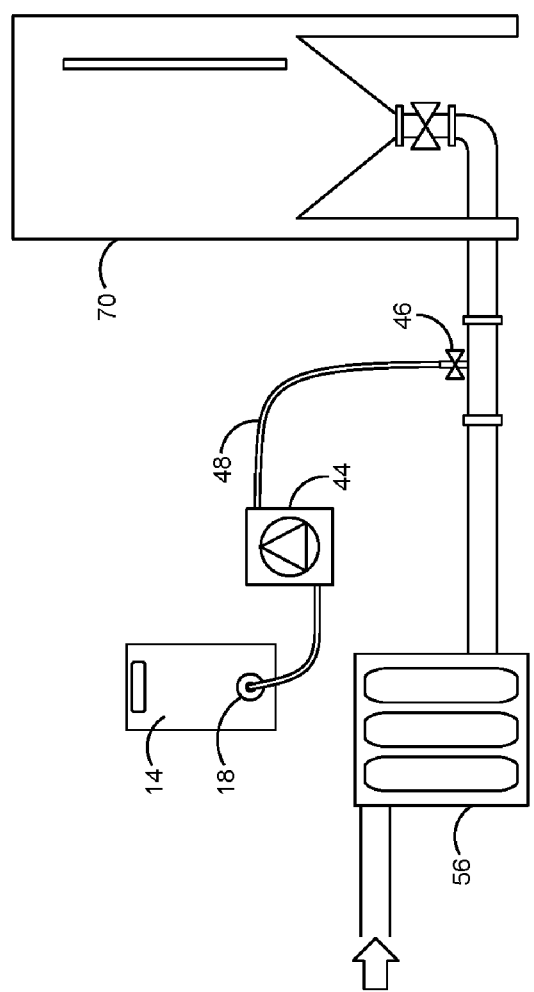
FIG. 5 is a schematic of the yeast vessel and liquid yeast transfer method including yeast vessel connection means, yeast vessel storage means, peristaltic brew pump, fermentor, and additional elements in an assembled configuration.
Figure 6:
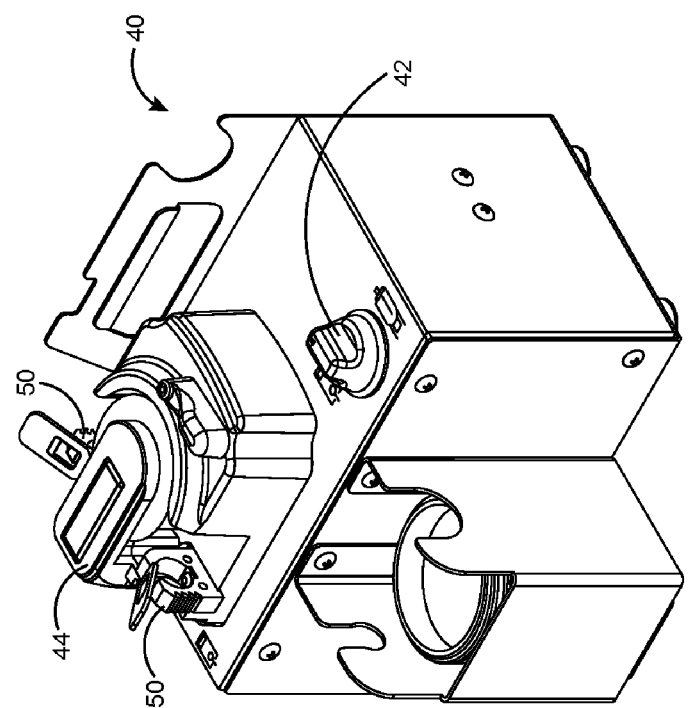
FIG. 6 is a perspective view of the peristaltic brew pump.

As described above, FIG. 5 shows the yeast vessel storage means 14, fermentor 70, connection means first opening 18, peristaltic brew pump body 40, pump initiation button 42, peristaltic brew pump 44, brewery line 48, and injector (or any sanitary connection) 46. The yeast pitching method of the present invention includes the steps of connecting an injector (or any sanitary connection) 46 to a brewery line 48 between the fermentor 70 and a peristaltic brew pump 44, downstream of the heat exchanger 56, fixing an sanitary connection tube to the peristaltic brew pump 44 and clamp 50, connecting a cap adapter to the yeast connection means 12 and opening the valve (not pictured), homogenizing the yeast, connecting the cap adapter (not pictured) to the yeast connection means 12, engaging the peristaltic brew pump 44 in the forward flow direction in order to transfer the yeast into the brewery line 48, engaging the peristaltic brew pump in the reverse flow direction to back flush the yeast vessel, and re-engaging the pump in the forward flow direction in order to transfer the yeast back into the brewery line 48. When these steps are complete, the valve may be closed and the brewery line 48 may be removed. As shown in FIG. 6, in some embodiments the invention includes a peristaltic brew pump 44, brew pump body 40, clamp 50, pump initiation button 42, and other common structural elements. In some embodiments, the pump includes a modified clamp adapted to secure a brewery line 48.

In some embodiments, an exterior wall of the yeast storage means serves as a resilient surface for direct ink printing and/or adhesive labeling, including the printing of QR codes and cell count information specific to each yeast vessel 10. In other embodiments, the walls of the yeast storage means include a material selected from the group consisting of polyurethane, laminated polyethylene, polyolefin, ethylene-vinyl acetate copolymer, polyvinylidene chloride, and/or a coextrusion of polyethylene and polyvinylidene chloride.

In some embodiments, a yeast pitching method includes the steps of connecting an injector (or any sanitary connection) 46 to a brewery line 48 between the fermentor and a peristaltic brew pump 44, fixing a sanitary connection tube to the peristaltic brew pump 44, connecting a cap adapter to the yeast connection means 12 and opening the valve, homogenizing the yeast following connection of the cap adapter to the yeast connection means 12, engaging the peristaltic brew pump 44 in the forward flow direction in order to transfer the yeast into the brewery line 48, engaging the peristaltic brew pump 44 in the reverse flow direction to back flush the yeast vessel 10, and re-engaging the pump 44 in the forward flow direction in order to transfer the yeast back into the brewery line 48. During the back flushing step, wort is introduced to the yeast slurry in order to alter its viscosity for ease of transfer. Preferably, the viscosity of the yeast slurry is lowered once it is homogenized with the wort. When these steps are complete, the valve may be closed and the brewery line 48 may be removed. In some embodiments, a vacuum is fixed to the yeast vessel 10 and/or brewery line 48 to remove excess oxygen. In other embodiments, nitrogen or another inert gas is injected into the yeast vessel 10 and/or brewery line 48 before transferring the yeast in order to improve glycogen conditions and yeast health. In some embodiments, pumping will continue to pull a vacuum until the operator stops it in order to ensure complete clearance of yeast from the brewery line 48. The clamp may also acts as a vacuum stop in order to prevent the wort from transferring back when the machine is not in operation.

Figure 7:
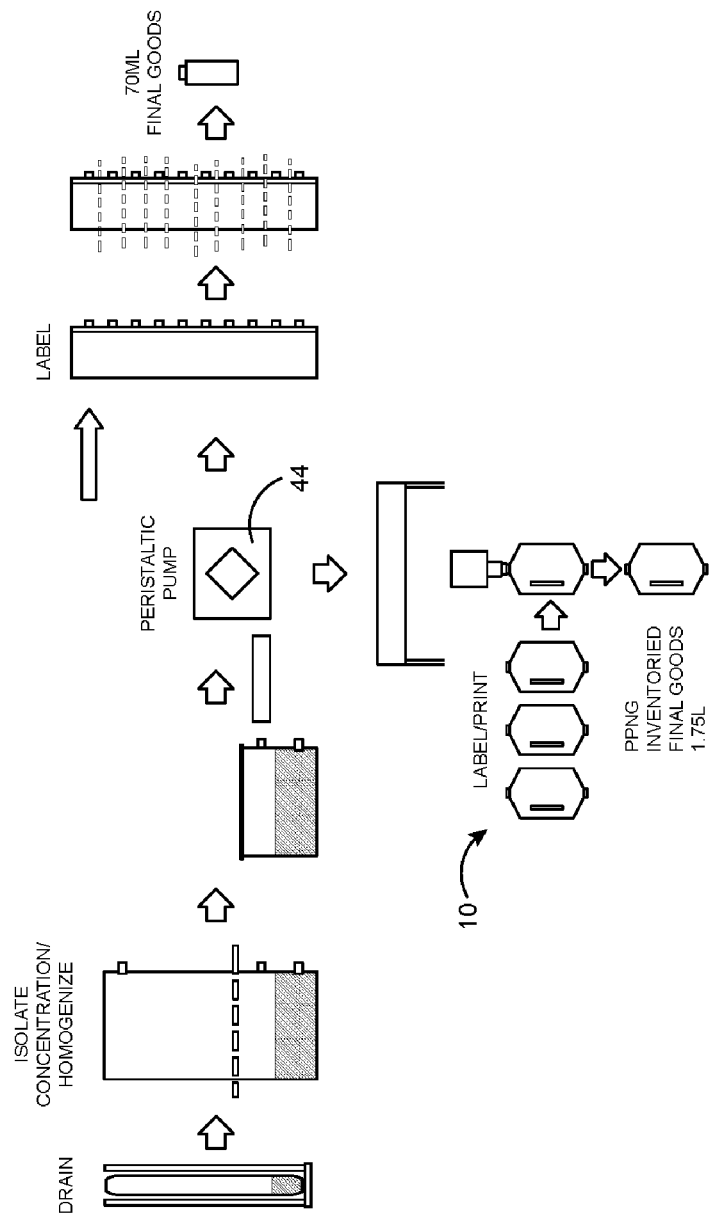
FIG. 7 is a diagram illustrating a disclosed transfer method including draining, homogenization, pumping, labeling, and packaging steps.

In some embodiments, the above steps are performed in the reverse order such that a fermentation product is recovered from the fermentor, enabling packaging and/or analysis of said fermentation product. In some embodiments, isopropyl alcohol is used to sterilize the yeast connection means 12 and other surfaces throughout the pitching process. In some embodiments, the rollers utilized in the peristaltic brew pump 44 are optimized to enhanced wort mixing and transfer time. In other embodiments, fermentation product and/or liquid yeast may be transferred from the peristaltic brew pump 44 to an empty yeast vessel 10 within a hood. Notably, FIG. 7 shows a schematic of one embodiment of a transfer process including draining, homogenization, pumping, labeling, and packaging steps.

As described above, homogenization is accomplished by re-engaging the pump 44 in the forward direction in addition to periodically manually manipulating the yeast. In some embodiments, a hose end of the injector 46 may be fixated to the peristaltic brew pump 44 with a zip tie, clamp, or the like. In some embodiments, a hose end of the injector is fixated to the peristaltic brew pump. A particular example of peristaltic pumping is herein disclosed, though the skilled artisan could substitute other pumps known in the art for use in this system.

In some embodiments, the transfer method includes both forward and reverse functions. In some embodiments, a user runs the brewery line 48 through the clamp, which then closes down on the clamp, and then pushes fluid through the brewery line 48 either in the forward direction for transferring the contents of the vessel into the brewery line 48 or in the reverse direction back through the brewery line 48 to achieve backflushing of the wort into the yeast vessel 10. In another embodiment, the pump automatically stops upon release of the brewery line 48, thus preventing accidental backflushing. In some embodiments, the sanitary tubing may be connected to a TC type connection to the brewery line (e.g., with tri clamp T). In embodiments, this connection is assembled proximal to a fermentor sight glass. In other embodiments, this connection is assembled proximal to the injector (or any sanitary connection) in order to allow improved flow into the transfer line. In some embodiments, the injector reduces the backpressure from about 6 psi to about 2 psi, thereby facilitating faster transfers. In other embodiments, the injector reduces the backpressure from about 10 psi to about 3 psi, thereby facilitating faster transfers.

In some embodiments, the brewery line 48 includes a swivel connected attachment, such that a connector swings free of the brewery line 48 and the yeast vessel 10. In some embodiments, a breathable cap is used to release large amounts of gas buildup. In the event of a large buildup of carbon dioxide ("$CO_2$"), this mechanism will quickly release a large amount of gas in a one way direction.

In other embodiments, the yeast storage means includes an external structural layering including at least four layers of film. In one embodiment, layers 1 and 4 (inner and outer) are 3 mil Polyester/polyethene (PE/PET) laminations with laser perforation to allow $CO_2$ that has passed through the inner layer to vent out of the outer layer, to minimize the ingress of oxygen back into the yeast vessel 10. In other embodiments, laser perforations include perforations set 5 mm apart and set up in a grid across the bag. In some embodiments, layers 2-3, the inner layers, are 1.5 mil PE, a highly breathable water-tight film allowing for breathability of the yeast during normal storage. This material also allows the slow release of any $CO_2$ buildup that continues to occur as a result of yeast metabolism.

In some embodiments, the structural layering of the yeast storage means includes a liquid tight structure with a high gas transference potential. In other embodiments, expanding $CO_2$ can pass through layers 2 or 3 to the chamber between layers 1 and 2 (front) or 3 and 4 (back) where the film has laser perforations that allow gas to the bleed out to the outer environment. As described above, a sightglass may be included proximal to the pump or transfer vessel to allow the brewer to see the color of wort transferring from the brew system to the fermentor. This element also allows the brewer to see the yeast entering the wort.

In view of the above detailed description, the herein described apparatus and transfer method allow for several additional advantages: a) maintenance of an anoxic (i.e., low oxygen) conditions during yeast transfer, thereby maximizing ethanol fermentation via anaerobic respiration, b) maintenance of an aseptic transfer environment due in part to the use of peristaltic pumps (e.g., because the motor components remain completely isolated from the tube interior), and c) improvements in the ease of yeast transfer (e.g., portability of the vessel/pump setup allows use with both large scale and small scale systems).

One of ordinary skill in the art will recognize that additional embodiments are also possible without departing from the teachings of the present invention or the scope of the claims which follow. This detailed description, and particularly the specific details of the exemplary embodiments disclosed herein, is given primarily for clarity of understanding, and no unnecessary limitations are to be understood therefrom, for modifications will become obvious to those skilled in the art upon reading this disclosure and may be made without departing from the spirit or scope of the claimed invention.

Although the invention has been shown and described with respect to a certain preferred embodiments, it is obvious that equivalent alterations and modifications will occur to others skilled in the art upon the reading and understanding of this specification and the annexed drawings. In particular regard to the various functions performed by the above described elements, the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any particular application.

What is claimed is:

1. A yeast vessel, comprising:
   a yeast connector, and yeast storage bag;
   said yeast storage bag comprising yeast storage bag walls and a yeast storage bag periphery, the yeast storage bag walls having an external structural layering and an internal structural layering, the yeast storage bag periphery including laser perforations that blends the external structural layering and the internal structural layering, allows $CO_2$ to vent out of the yeast vessel, minimizes the ingress of oxygen back into the yeast vessel and allows the yeast vessel to function under repeated fluctuations in pressure and temperature;
   the yeast storage bag walls further comprising PET laminate materials;
   said yeast connector further comprising a cap adapter; and
   said yeast connector comprising at least one port having an opening and a filter in sealing engagement with the port adapted to support an aseptic transfer of liquid yeast under a range of temperature and pressure conditions, the port adapted to reseal the yeast vessel under aseptic conditions, permitting semi-permeable efflux of carbon dioxide out of the yeast vessel.

2. The yeast vessel of claim 1, wherein the internal structural layering includes clear LDPE.

3. The yeast vessel of claim 1, wherein the external structural layering including 6 mil PET laminate.

4. The yeast vessel of claim 1, wherein the yeast storage bag is adapted to store a quantity of liquid yeast ranging between 500 ml and 3 L, preferably between 1 L and 2 L.

5. The yeast vessel of claim 2, wherein the unidirectional valve is semi-permeable to carbon dioxide, permitting carbon dioxide egress out of the yeast vessel.

6. The yeast vessel of claim 1, wherein the walls of the yeast storage bag are comprised of material selected from the group consisting of polyurethane, laminated polyethylene, polyolefin, ethylene-vinyl acetate copolymer, polyvinylidene chloride, and/or a coextrusion of polyethylene and polyvinylidene chloride.

7. A yeast vessel, comprising:
   a yeast storage bag comprising yeast storage bag walls and a yeast storage bag periphery, the yeast storage bag walls having an external structural layering and an internal structural layering, the yeast storage bag periphery including laser perforations that blends the external structural layering and the internal structural layering, allows $CO_2$ to vent out of the yeast vessel, minimizes the ingress of oxygen back into the yeast vessel and allows the yeast vessel to function under repeated fluctuations in pressure and temperature;
   a yeast connector;
   the yeast connector and yeast storage bag support aseptic yeast transfer into fermentors;
   the yeast connector and yeast storage bag remaining fully functional following more than one hundred transfer cycles and under low pressure conditions, the yeast storage bag having yeast storage vessel walls further comprising PET laminate, said yeast connector comprising at least one port adapted to reseal the yeast vessel under aseptic conditions; and
   a valve in cap engagement with the at least one of the port, the valve allowing egress of fermentation gases, thereby enhancing yeast health and minimizing contamination by microorganisms.

8. The yeast vessel of claim 7, comprising an inside surface of the at least one port defining an opening, and means of connection to quick connect fittings for engagement with ½" silicone tubing to support aseptic transfer of liquid yeast to a fermentor under a range of temperature and pressure conditions common to standard brewing operations.

9. The yeast vessel of claim 7, further comprising a filter of temperature-resistant, pressure-resistant, chemically resilient, and/or electrochemically resilient materials, thereby supporting aseptic transfer of liquid yeast to a fermentor.

10. The yeast vessel of claim 7, the yeast storage bag and yeast connector further comprising:
    a yeast storage bag nonporous top surface and bottom surface, a first opening in said top surface;
    the valve and/or filter disposed over said first opening, permitting escape of fermentation gases from said yeast vessel, said first opening having a Gurley porosity in the range of 2 to 120 seconds and disposed such that the egress of all gases from said yeast vessel during fermentation must pass through said first opening;
    a liquid inlet means disposed over said second opening, providing a means of liquid flow into said yeast vessel;
    a bottom opening in said bottom surface;
    liquid outlet means disposed over said bottom surface opening, providing a liquid outlet from the yeast vessel; and
    a cap adapter providing a reversible means of transferring out of and into the yeast vessel.

11. The yeast vessel of claim 10, wherein a filled yeast vessel comprises at least 1 billion yeast cells/ml, preferably 2 billion yeast cells/ml.

* * * * *